(12) United States Patent
Demir

(10) Patent No.: US 11,185,420 B2
(45) Date of Patent: Nov. 30, 2021

(54) EXPANDABLE CAGE

(71) Applicant: TOBB EKONOMI VE TEKNOLOJI UNIVERSITESI, Ankara (TR)

(72) Inventor: Teyfik Demir, Ankara (TR)

( * ) Notice: Subject to any disclaimer, the term of this patent is extended or adjusted under 35 U.S.C. 154(b) by 326 days.

(21) Appl. No.: 16/473,043

(22) PCT Filed: Dec. 28, 2017

(86) PCT No.: PCT/TR2017/050713
§ 371 (c)(1),
(2) Date: Jun. 24, 2019

(87) PCT Pub. No.: WO2018/208268
PCT Pub. Date: Nov. 15, 2018

(65) Prior Publication Data
US 2021/0275315 A1    Sep. 9, 2021

(30) Foreign Application Priority Data

Dec. 30, 2016    (TR) .................................. 2016/20372

(51) Int. Cl.
*A61F 2/44* (2006.01)
*A61F 2/30* (2006.01)

(52) U.S. Cl.
CPC .......... *A61F 2/442* (2013.01); *A61F 2/30771* (2013.01); *A61F 2/4455* (2013.01);
(Continued)

(58) Field of Classification Search
CPC .......... A61F 2/44; A61F 2/442; A61F 2/4455; A61F 2/446; A61F 2/4465; A61F 2/447
See application file for complete search history.

(56) References Cited

U.S. PATENT DOCUMENTS 6,159,244 A * 12/2000 Suddaby ............... A61F 2/4611
  623/17.11
6,332,895 B1 * 12/2001 Suddaby ............... A61F 2/4455
  623/17.11
(Continued)

FOREIGN PATENT DOCUMENTS

CN    106166092 A1    11/2016
TR    2008/04254 A1    6/2008
(Continued)

OTHER PUBLICATIONS

International Search Report for corresponding PCT/TR2017/050713.

*Primary Examiner* — Eric S Gibson
(74) *Attorney, Agent, or Firm* — Egbert, McDaniel & Swartz, PLLC

(57) ABSTRACT

An expandable cage which is used in spinal surgery and which allows adjustment of distance between two vertebrae in which it is placed as preferred. An expandable cage-basically includes at least one body which is located in emptied area between damaged vertebrae during the surgical procedure and serves as a disc; and at least one movable element which is located on the body and is fitted in the opening made in the body by means of the retainers disposed at the sides thereof; which has a toothed surface contacting with the upper vertebra and being attached to it; and the height of which can be adjusted by pushing the protrusion provided in the lower portion thereof according to the intervertebral distance of patient by means of the expansion apparatus.

15 Claims, 5 Drawing Sheets

Figure 1:
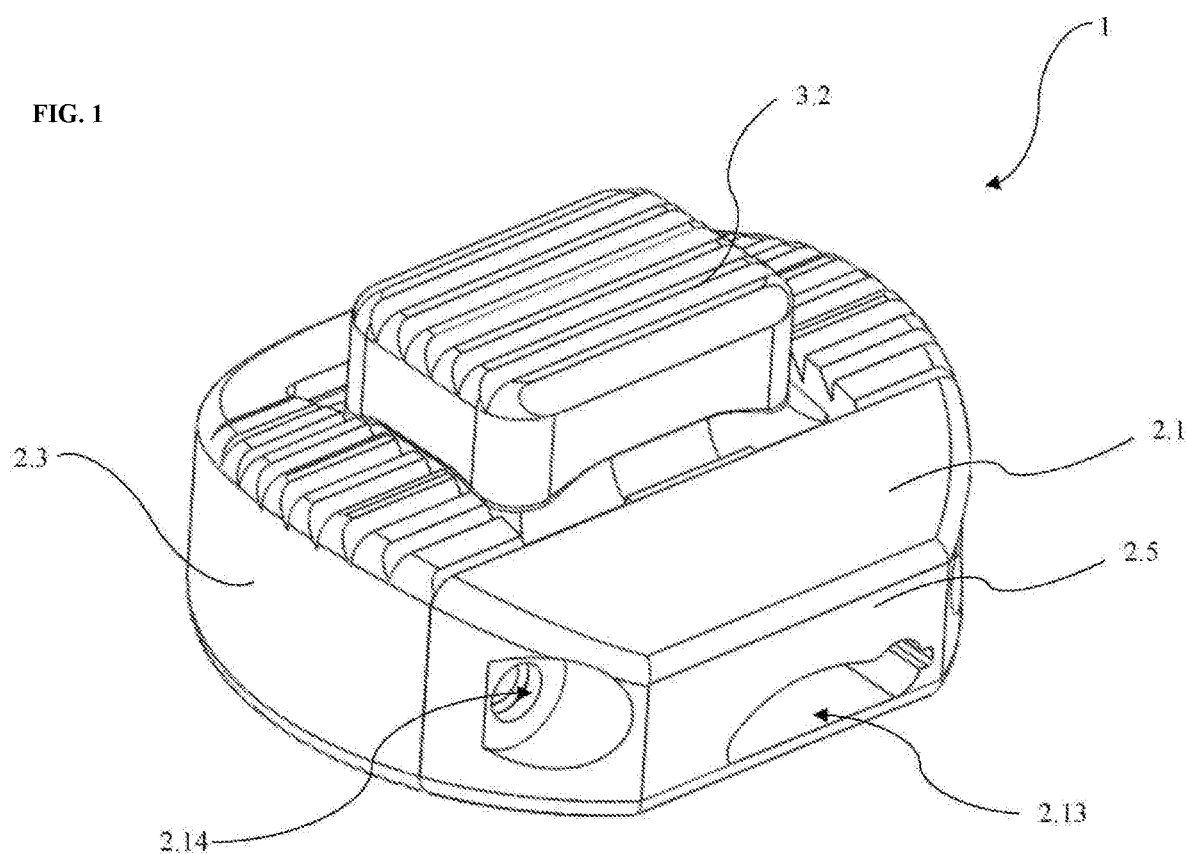

(52) U.S. Cl.
CPC ............ *A61F 2002/30482* (2013.01); *A61F 2002/30556* (2013.01); *A61F 2002/30579* (2013.01); *A61F 2002/30904* (2013.01)

(56) References Cited

U.S. PATENT DOCUMENTS

| | | | | |
|---|---|---|---|---|
| 6,562,074 | B2* | 5/2003 | Gerbec | A61F 2/4611 623/17.15 |
| 7,094,257 | B2* | 8/2006 | Mujwid | A61F 2/447 623/17.15 |
| 8,715,351 | B1* | 5/2014 | Pinto | A61F 2/447 623/17.15 |
| 9,050,194 | B2* | 6/2015 | Thibodeau | A61F 2/30771 |
| 9,233,007 | B2* | 1/2016 | Sungarian | A61F 2/442 |
| 9,364,344 | B2* | 6/2016 | Whipple | A61F 2/4455 |
| 9,532,883 | B2* | 1/2017 | McLuen | A61F 2/4657 |
| 9,566,167 | B2* | 2/2017 | Barrus | A61F 2/4465 |
| 9,603,715 | B2* | 3/2017 | Thibodeau | A61F 2/442 |
| 9,820,866 | B2* | 11/2017 | Whipple | A61F 2/4657 |
| 10,010,429 | B2* | 7/2018 | Dmuschewsky | A61F 2/447 |
| 10,092,416 | B2* | 10/2018 | Davis | A61F 2/447 |
| 10,159,583 | B2* | 12/2018 | Dietzel | A61F 2/4657 |
| 10,292,830 | B2* | 5/2019 | McLuen | A61F 2/442 |
| 10,413,419 | B2* | 9/2019 | Thibodeau | A61F 2/4611 |
| 10,420,654 | B2* | 9/2019 | Logan | A61F 2/4465 |
| 10,463,501 | B2* | 11/2019 | Black | A61F 2/4455 |
| 10,548,738 | B2* | 2/2020 | Milz | A61F 2/4455 |
| 10,940,018 | B2* | 3/2021 | Sharifi-Mehr | A61F 2/447 |
| 2004/0162618 | A1* | 8/2004 | Mujwid | A61F 2/447 623/17.15 |
| 2009/0164017 | A1* | 6/2009 | Sommerich | A61F 2/44 623/17.16 |
| 2010/0280616 | A1* | 11/2010 | Frasier | A61F 2/4611 623/17.16 |
| 2010/0286779 | A1* | 11/2010 | Thibodeau | A61F 2/4611 623/17.11 |
| 2010/0292796 | A1* | 11/2010 | Greenhalgh | A61B 17/8858 623/17.11 |
| 2012/0143341 | A1* | 6/2012 | Zipnick | A61B 17/7067 623/17.16 |
| 2013/0158669 | A1* | 6/2013 | Sungarian | A61F 2/447 623/17.16 |
| 2013/0204371 | A1* | 8/2013 | McLuen | A61F 2/442 623/17.16 |
| 2013/0274883 | A1* | 10/2013 | McLuen | A61F 2/28 623/17.16 |
| 2014/0188225 | A1* | 7/2014 | Dmuschewsky | A61F 2/442 623/17.16 |
| 2014/0277051 | A1 | 9/2014 | Sanderson | |
| 2014/0277501 | A1* | 9/2014 | Northcutt | A61F 2/447 623/17.16 |
| 2015/0230930 | A1* | 8/2015 | Thibodeau | A61F 2/4465 623/17.16 |
| 2017/0112632 | A1* | 4/2017 | Dmushewsky | A61F 2/4455 |
| 2017/0119542 | A1* | 5/2017 | Logan | A61F 2/442 |
| 2017/0119543 | A1* | 5/2017 | Dietzel | A61F 2/4657 |
| 2017/0151066 | A1* | 6/2017 | Thibodeau | A61F 2/442 |
| 2017/0290671 | A1* | 10/2017 | Milz | A61F 2/4425 |
| 2019/0374345 | A1* | 12/2019 | Thibodeau | A61F 2/44 |
| 2021/0068959 | A1* | 3/2021 | McLuen | A61F 2/4455 |
| 2021/0068973 | A1* | 3/2021 | McLuen | A61F 2/4611 |

FOREIGN PATENT DOCUMENTS

| | | |
|---|---|---|
| TR | 2009/03712 U | 5/2009 |
| WO | 2010129697 A1 | 11/2010 |
| WO | 2015134195 A1 | 9/2015 |

* cited by examiner

EXPANDABLE CAGE

FIELD OF THE INVENTION

The present invention relates to an expandable cage which is used in spinal surgery, is located between the vertebrae during the operation, and preserves the distance between the vertebrae as desired.

BACKGROUND OF THE INVENTION

Herniated disc and cervical disc hernia result from displacement of the cartilage (disc) between the vertebrae towards the ependymal canal, and thus applying pressure on the nerves and on the spinal cord.

It is typically sufficient, for the diagnosis and identifying the location of the disk herniation, to carefully examine any loss of strength, loss of sense or abnormal reflex in addition to a clinical evaluation for determining the type and location of the pain. As a result of herniation, acute pain and loss of sense may occur in the area of the hernia. It is only possible with surgical intervention to eliminate such pain and loss of sense in some patients. In parallel with the advances in technology, cervical disc hernia surgery can be performed in smaller spaces than before. The patients are operated through anterior or posterior cervical spine. In case of operations through the anterior cervical spine, the region between two vertebrae is emptied and the disc between said vertebrae is removed, and subsequent to cleaning this region, a cage, into which bone graft is added and which prevents collapse between the vertebrae, is located. The cage configurations used in the state of the art are typically sized by taking the distance between the vertebrae of the patient as an average. However, the provision of cage configurations with adjustable height is crucial since the anatomy and vertebral column length differ from one patient to another. Such cage configurations can be made of various materials, particularly of metal, carbon, and polyetheretherketone (PEEK).

The most important problems in relation to the cage configurations used in surgical applications in the state of the art are: the inability to adjust the cages according to the height of the patient, to determine the graft amount to be put in the cage, and to locate the cage between the vertebrae.

The Turkish Patent Application No. TR200804254 in the state of the art discloses a cervical disc prosthesis. The prosthesis mentioned in this document is a cervical disc prosthesis which is used in neck region and allows rotating the neck; which has a circular upper body and lower body that operate together under the compression effect at the bone interval to which they are engaged; and which comprises at least one connector which engages said upper body and lower body and is formed on said upper body or lower body such that said cervical disc will operate together independent of the bone compression, and at least one movement space which is located in the middle portion of the upper body or lower body. Said prosthesis consists of two pieces and it is mounted by the interconnection of said two pieces by means of a screw. The fact that the prosthesis consists of two pieces results in the duration of the operation to be longer during surgical procedure; moreover, the used connection means may damage to the patient's body after the implementation. In the present invention, however, the cervical cage has a single body and its size can be varied during the operation by expanding by way of the movable element located thereon. Hence, it can be readily used in all cervical applications, being expanded and contracted in accordance with the bone length of the patient.

The Turkish Utility Model document No. TR200903712 discloses implants (hard materials placed in the body for treatment purposes by making use of surgical methods) used in spinal surgery operations in health sector. The present invention particularly relates to an excage expandable cervical device which has been developed for use in the treatment of several spinal problems, e.g. degenerative spondylolisthesis, stenosis, spinal injuries and spinal discopathies; which allows preserving the required height between the discs; and which comprises dowel pins and an ejector pin with locking property. The invention described in this document consists of lower and upper bodies that are manufactured in an integrated manner. The invention is disadvantageous in that the height cannot be adjusted as desired during the implementation. Further, the bone graft amount to be put in the implant cannot be adjusted during the implementation, either. In case of failing to put bone graft in the implant in a sufficient amount, it takes longer for the patient to recover; at the same time the desired healing cannot be achieved. In the present invention, however, the movable element disposed in the excage expandable cervical device is raised by means of an expansion apparatus during surgery, and thus allows adjusting the distance between the vertebrae of the patient. In addition to this, since it has a closed body configuration, the bone graft to be placed in the cage is done so before the cage is located between the vertebrae. Hence, the duration of the operation becomes shorter, and at the same time the cage can be located between the vertebrae.

There exists no expandable cage configuration in the state of the art that preserves the distance between two vertebrae as preferred, can be implanted easily, does not cause any infection, and can be used in patients with different body and bone type.

OBJECTS OF THE INVENTION

The object of the present invention is to provide an expandable cage which fills in the area between the two vertebra in which it is applied, and is fused with the bones, and thus enables the patients to continue their daily lives shortly after the implementation.

Another object of the present invention is to provide an expandable cage the height of which can be adjusted by expanding precisely subsequent to being located between two vertebrae such that the desired size will be obtained.

Still another object of the present invention is to provide an expandable cage which does not cause any post-operative infection as it is produced of material that is compatible with the body, i.e. of biocompatible material.

Yet another object of the present invention is to provide an expandable cage that may be used in patients with different body and bone size.

Another object of the present invention is to provide an expandable cage which can be used in different surgical settings since it can be easily applied by means of an expansion apparatus during the operation.

Another object of the present invention is to provide an expandable cage that is capable of carrying post-implementation load at the application site due to the high resistance of the material which it is made of.

And another object of the present invention is to provide an expandable cage which makes the duration of the operation shorter due to the facilitated height adjustment.

SUMMARY OF THE INVENTION

An expandable cage which has been developed for achieving the objects of the present invention and is defined in the independent claim and other claims dependent thereon comprises: a body which has an upper surface with sparks and a lower surface with sparks thereon, said upper surface and lower surface being fitted on the upper vertebra and the lower vertebra respectively, and wherein the movable element is located in the opening comprised by the body; and a movable element which, subsequent to being located in the body, is capable of moving in upward direction and being locked, whereby it allows fixation at the desired height.

The opening made in the body is delimited by a front inner wall with a barrier thereon and a rear inner wall, by the side inner walls having lugs and inserts thereon, and by the lower inner wall presenting the base. When the movable element is located inside the body, it is fitted on the inserts in normal position (in non-elevated position). When the movable element is lifted as preferred, its lower portion and upper portion are delimited by the lugs and barriers respectively, and then being fitted in the emptied area disposed in the front inner wall. Thus, the movable element remains fixed inside the body at the preferred height.

DETAILED DESCRIPTION OF THE INVENTION

An expandable cage developed for achieving the objects of the present invention is illustrated in the accompanying drawings, in which;

FIG. 1. Perspective view of the expandable cage.

Figure 2:
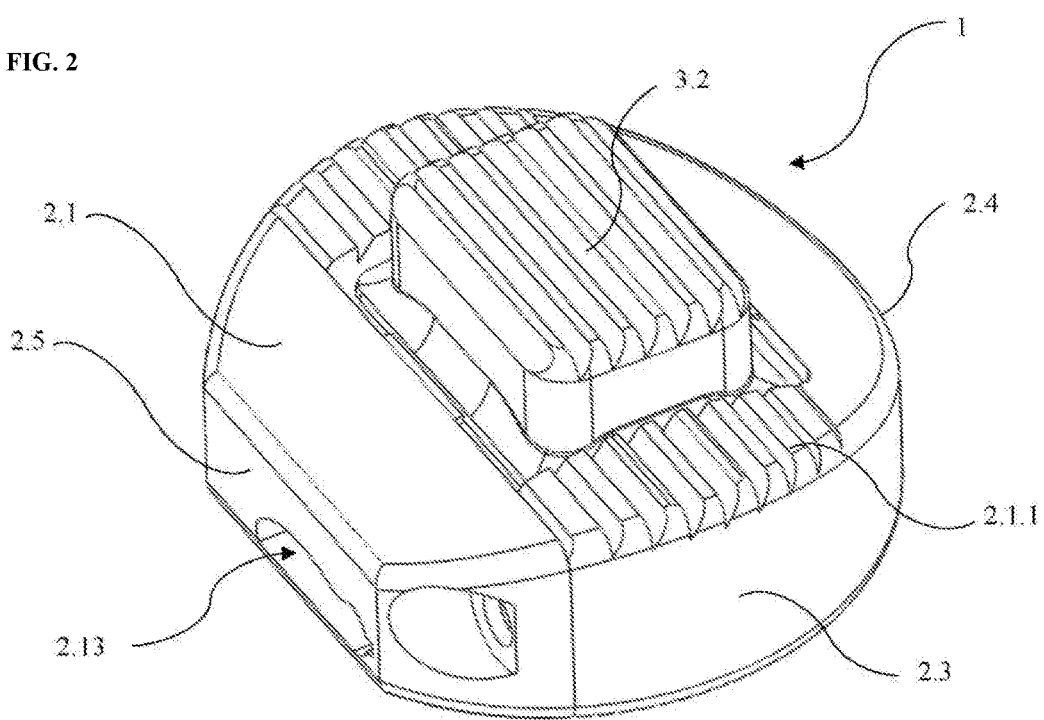

FIG. 2. Perspective view of the expandable cage from another angle.

Figure 3:
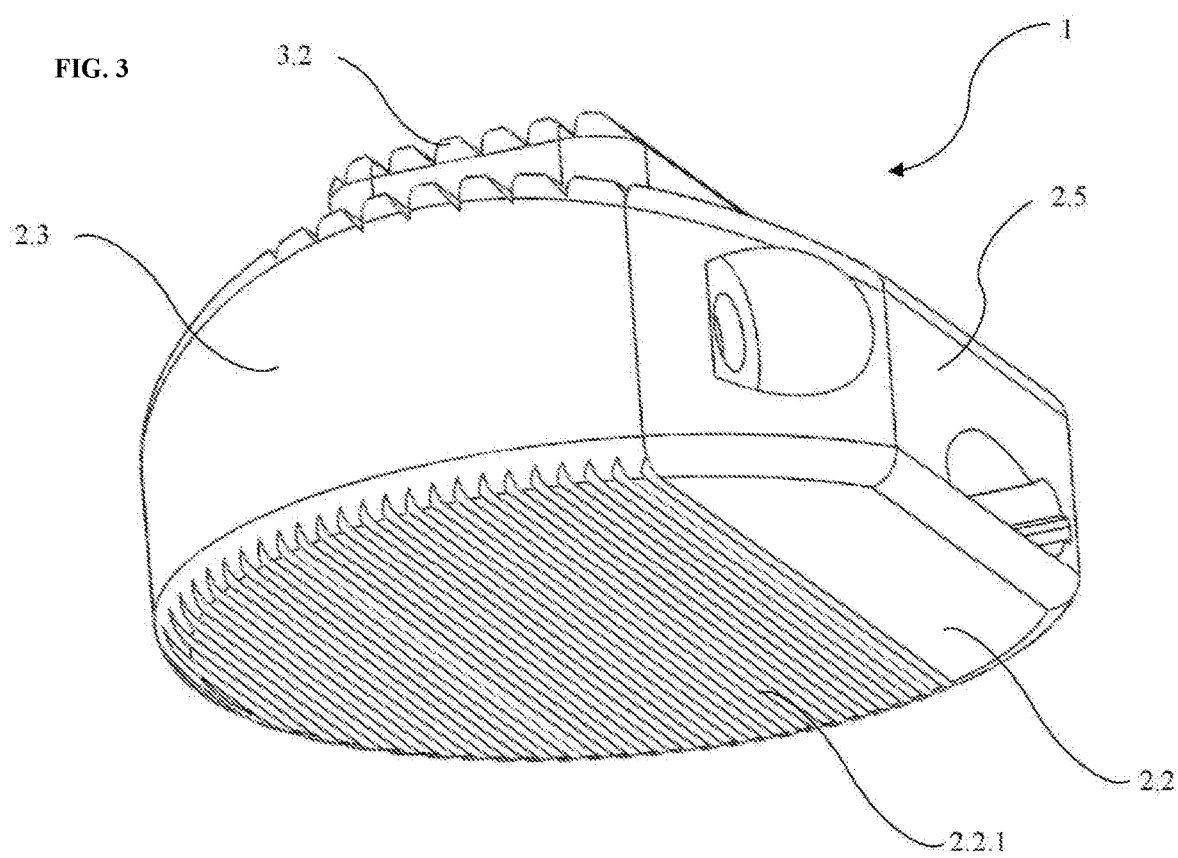

FIG. 3. Bottom perspective view of the expandable cage.

Figure 4:
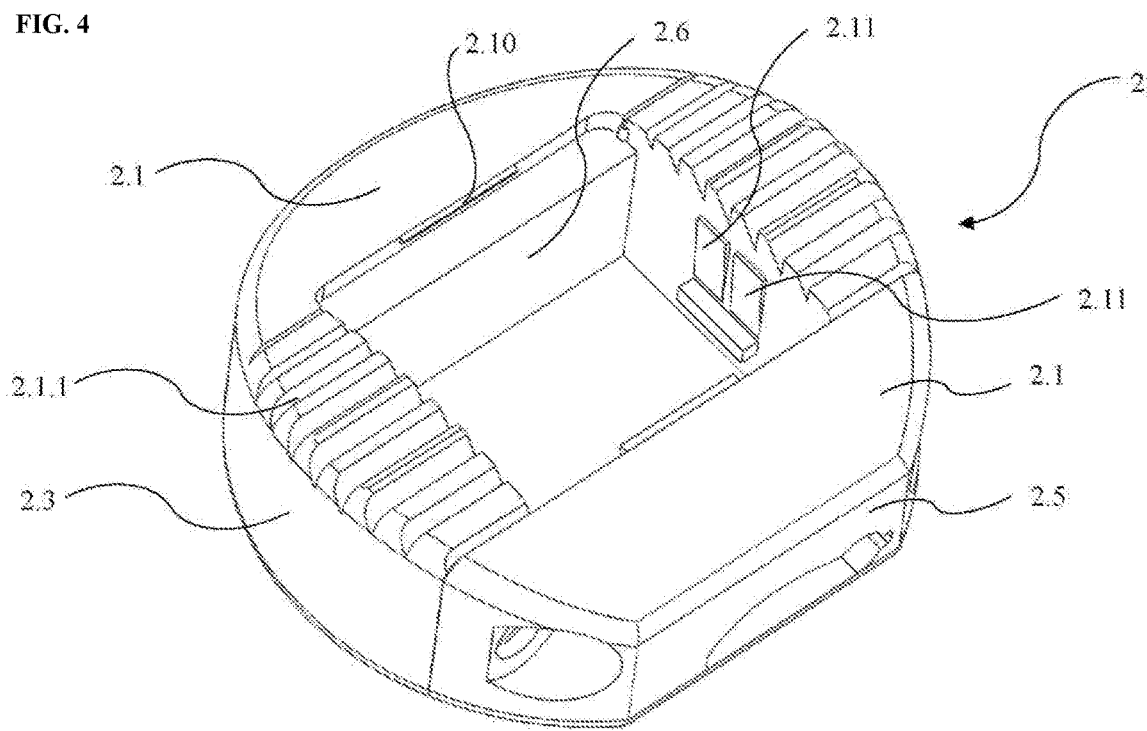

FIG. 4. Perspective view of the body.

Figure 5:
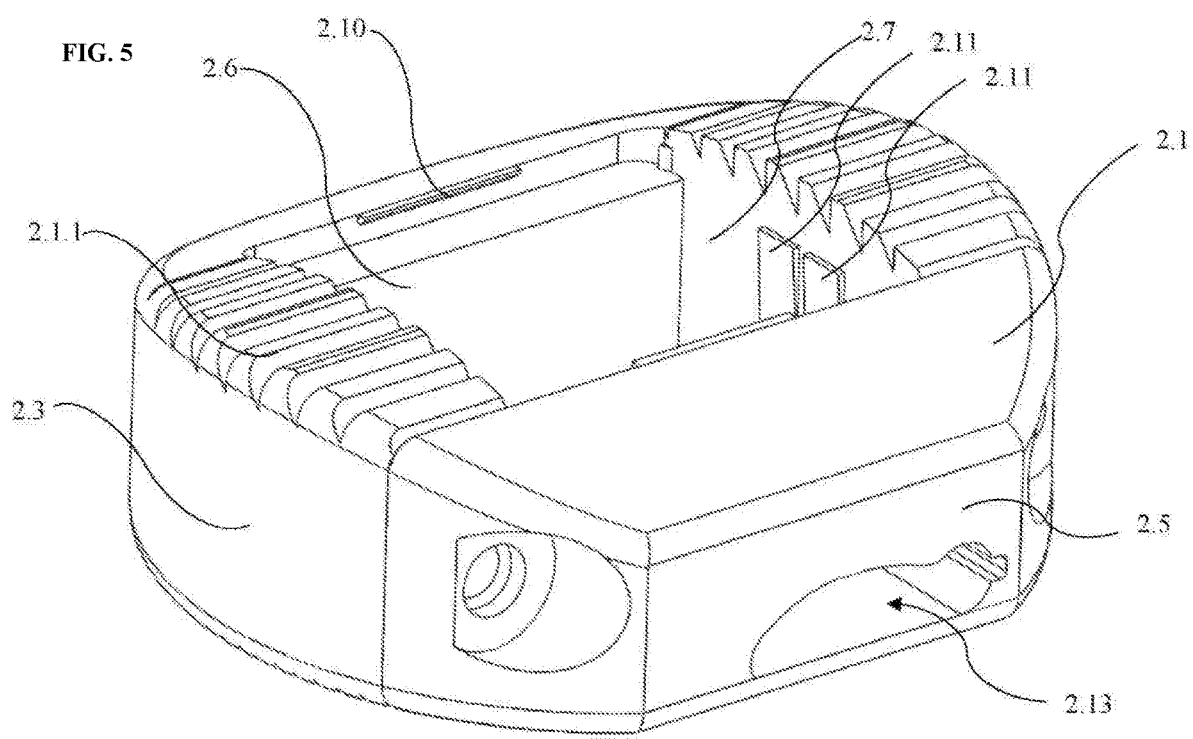

FIG. 5. Perspective view of the body from another angle.

Figure 6:
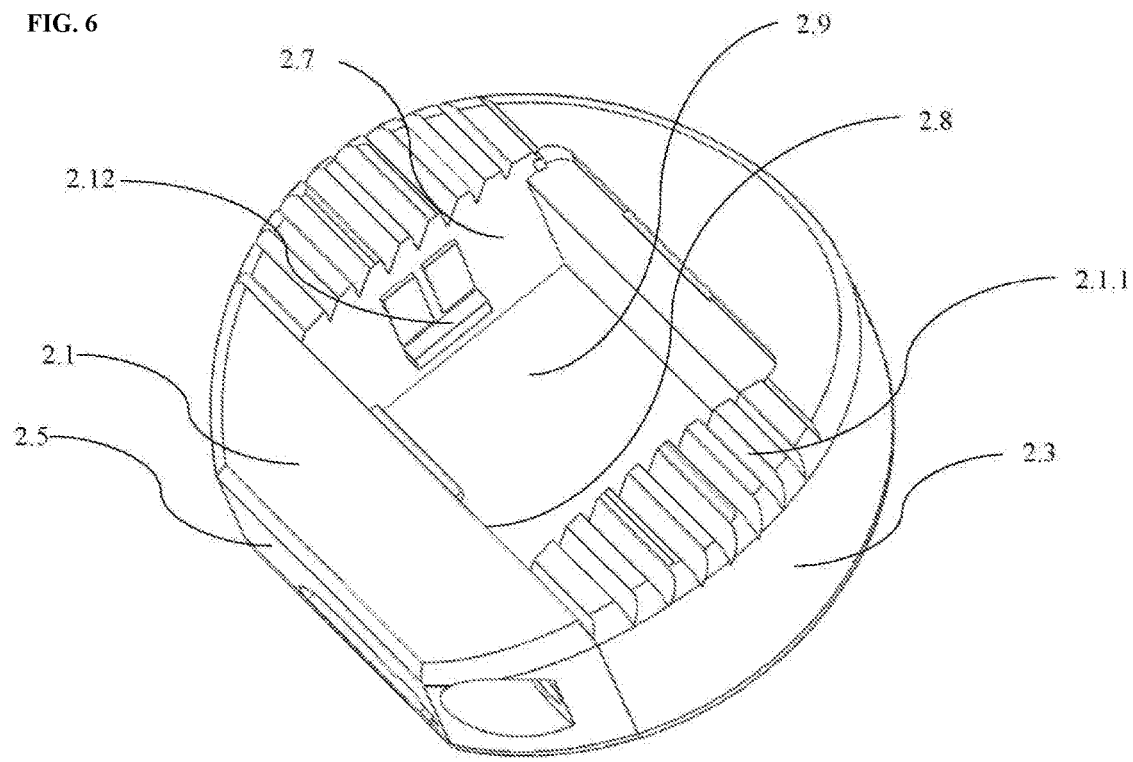

FIG. 6. Perspective view of the body from another angle.

Figure 7:
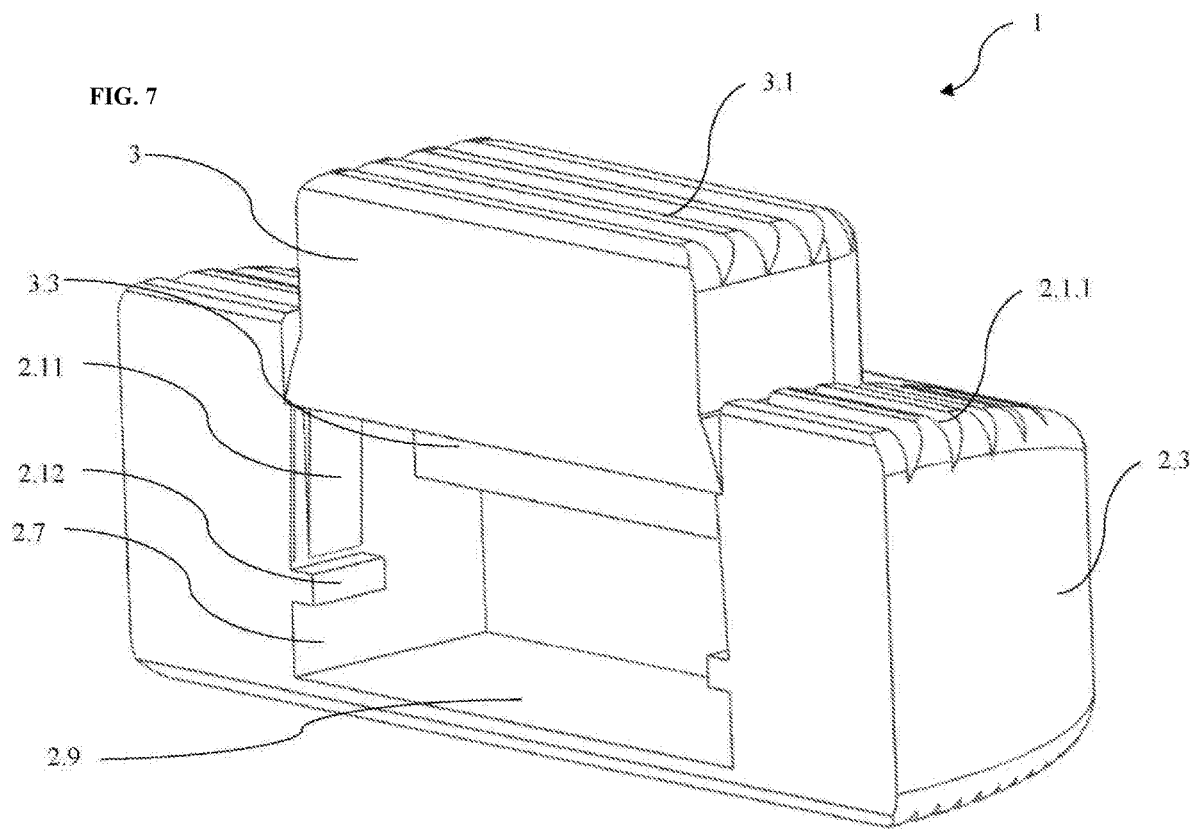

FIG. 7. Perspective cross-sectional view of the expandable cage.

Figure 8:
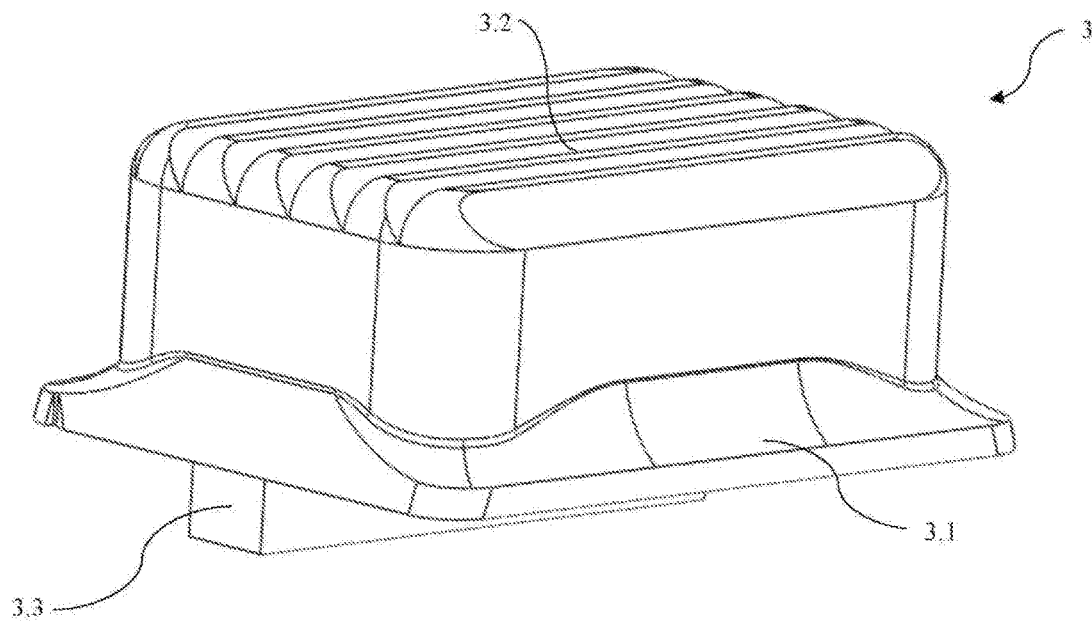

FIG. 8. Perspective view of the movable element.

Figure 9:
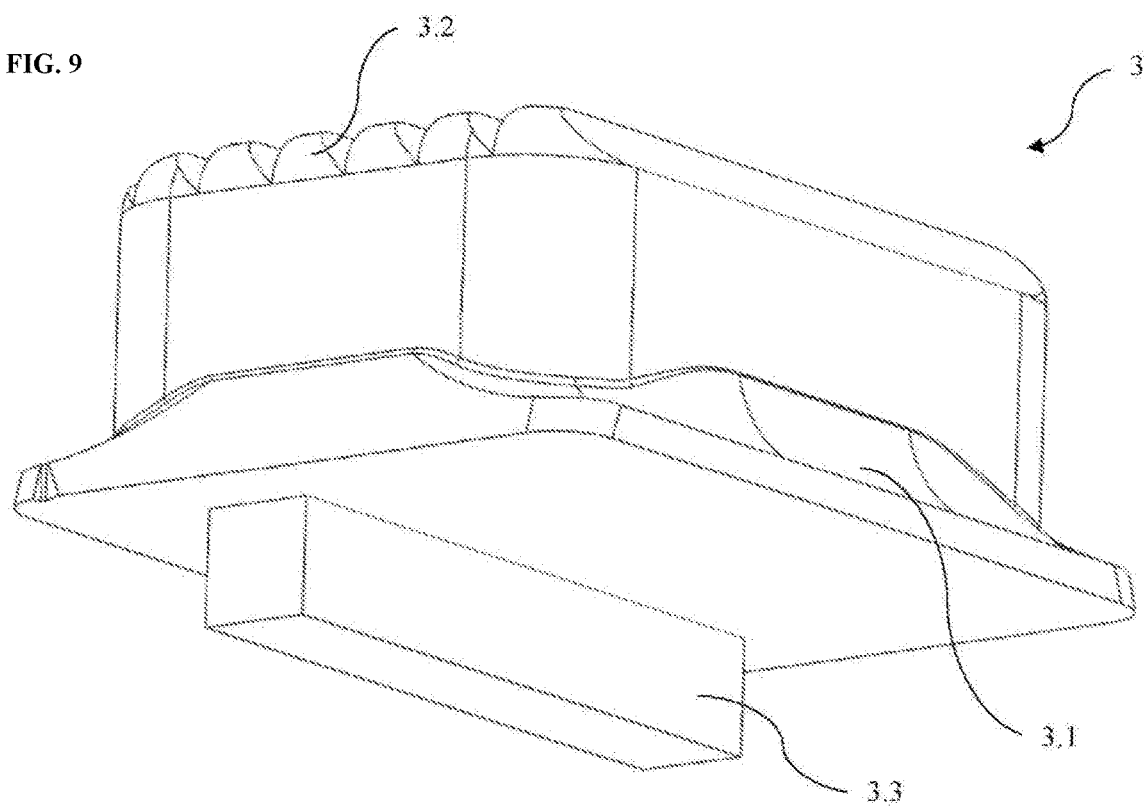

FIG. 9. Bottom perspective view of the movable element.

Figure 10:
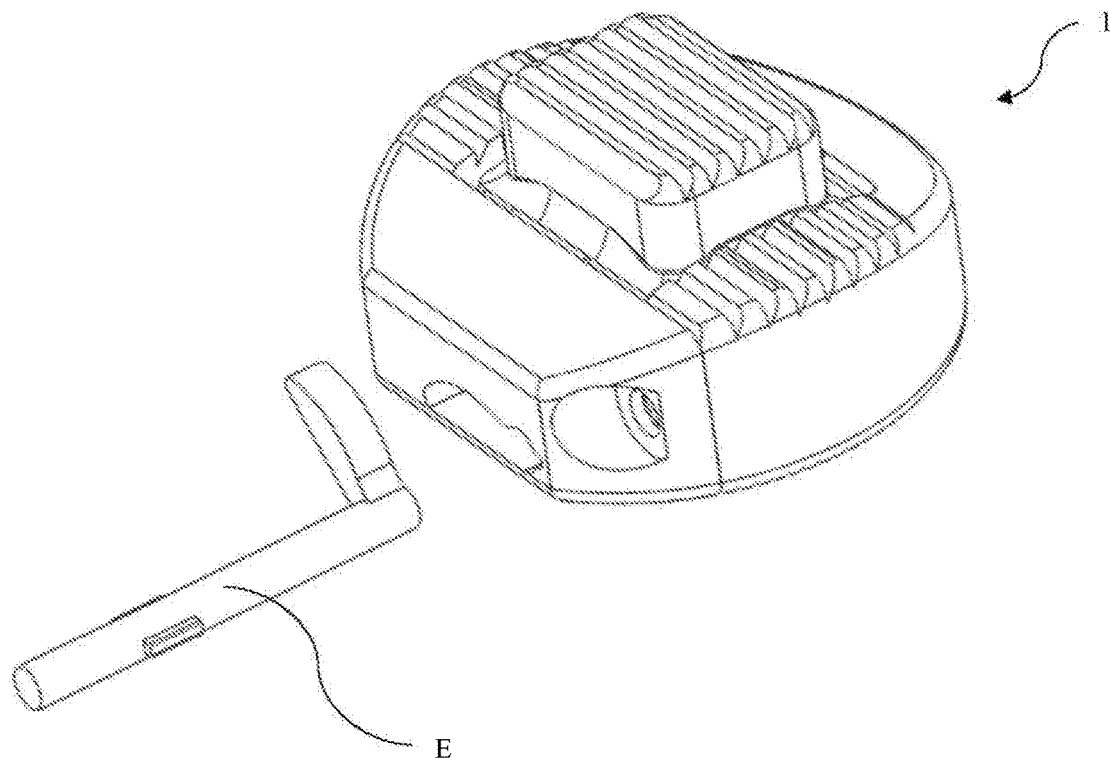

FIG. 10. Perspective view of the expandable cage and expansion apparatus.

The components in the drawings are enumerated individually and the reference numbers corresponding thereto are given below.

1. An expandable cage
2. Body
   2.1. Upper surface
      2.1.1. Spark
   2.2. Lower surface
      2.2.1. Spark
   2.3. Lateral surface
   2.4. Front surface
   2.5. Rear surface
   2.6. Front inner wall
   2.7. Side inner wall
   2.8. Rear inner wall
   2.9. Lower inner wall
   2.10. Barrier
   2.11. Lug
   2.12. Joint
   2.13. Inlet
   2.14. Horizontal hole
3. Movable element
   3.1. Retainer
   3.2. Toothed surface
   3.3. Protrusion A. Expansion apparatus An expandable cage (1) configuration that preserves the distance between two vertebrae as preferred during cervical surgical procedures, can be implanted easily, does not cause any infection, and can be used in patients with different body and bone type due to the height-adjustable structure thereof, basically comprises:

at least one body (2) which is located in the emptied area between the damaged vertebrae during the surgical procedure and serves as a disc, and at least one movable element (3) which is located on the body (2) and is fitted in the opening made in the body (2) by means of the retainers (3.1) disposed at the sides thereof; which has a toothed surface (3.2) contacting with the upper vertebra and being attached to it; and the height of which can be adjusted by pushing the protrusion (3.3) provided in the lower portion thereof according to the intervertebral distance of the patient by means of the expansion apparatus (E).

In an embodiment of the invention, there exists a body (2). The body (2) is located between the vertebrae and serves the same function as the damaged and removed disc. The body (2) mainly comprises at least one upper surface (2.1) fitted in the upper vertebra and having sparks (2.1.1) on the surface thereof, at least one lower surface (2.2) fitted in the lower vertebra and having sparks (2.2.1) on the surface thereof, lateral surfaces (2.3) provided at both sides of the body (2), at least one front surface (2.4) facing towards the inside of the body according to the vertebrae to which it is positioned, and at least one rear surface (2.5) facing towards the outside of the body according to the vertebrae to which it is positioned.

In order to locate the movable element (3), a portion of the body is emptied at sufficient dimensions such that the movable element (3) will be positioned therein. The emptied portion is provided with a front inner wall (2.6) which is arranged parallel to the front surface (2.4). The front inner wall (2.6) has a certain thickness in parallel to the front surface (2.4) and a height which is shorter than that of the front surface (2.4). One side of the movable element (3) is fitted in the space remaining between the front inner wall (2.6) and the front surface (2.4).

There exists a barrier (2.10) on the front inner surface (2.4) in the emptied area between the front inner wall (2.6) and the front surface (2.4). When the movable element (3) is raised, the retainer (3.1) disposed at its one side is engaged in said barrier (2.10).

In an embodiment of the invention, two opposed side inner walls (2.7) that are joined perpendicularly to the front inner wall (2.6) and rear inner wall (2.8) forming the emptied area within the body (2). The side inner walls (2.7) are arranged in parallel to the opposed lateral surfaces (2.3). The side inner wall (2.7) is preferably provided thereon with lugs (2.11) and inserts (2.12). The lug (2.11) disposed on the side inner wall (2.7) is the portion in which the movable element (3) is fitted at the preferred height (FIG. 7). In this embodiment of the invention, the side inner wall (2.7) is provided thereon with two lugs (2.1) which are preferably located adjacently. Moreover, the opposed side inner walls (2.7) are provided a total number of four lugs (2.11) thereon.

In another embodiment of the invention, the shape and dimensions of the lug (2.11) may vary according to the form of the lower surface of the movable element (3) located thereon. The lugs (2.11) stably maintains the movable element (2) at the preferred height. In this embodiment of the invention, the lug (2.11) is raised upwards from the lower portion of the side inner wall (2) at a certain angle and has a "cam" shape. In this embodiment of the invention, the lugs (2.11) are provided by shaping the side inner walls (2.7). In alternative embodiments of the invention, the lugs (2.11) are manufactured separately from the body (2) and may be mounted in the side inner walls (2.7).

In an embodiment of the invention, the insert (2.12) is disposed in the lower portion of the lugs (2.11) provided on the side inner walls (2.7). The insert (2.12) is arranged in the lower portion of the lugs (2.11) such that it will be perpendicular to the lugs (2.11) and parallel to the lower inner wall (2.9). The insert (2.12) is the portion in which the retainers (3.1) provided at the sides of the movable element (3) are fitted in the position where the movable element (3), which is placed in the emptied portion inside the body (2), is not preferred to be raised.

In an embodiment of the invention, there exists a rear inner wall (2.8) forming the emptied area within the body (2). The rear inner wall (2.8) is parallel to the rear surface (2.5) and provided thereon with a barrier (2.10). The retainer (3.1) disposed at one side of the movable element (3), which is preferred to be raised during the surgical operation, is fitted in the space between the front inner wall (2.6) and front surface (2.4), and then engaged in the barrier (2.10) provided thereon as well as in the barrier (2.10) on the rear inner wall (2.8) opposite said barrier (2.10). The barriers (2.10) hinder the upward movement of the retainers (3.1) from the upper portions thereof, and thus maintaining the movable element (3) at the preferred height stably.

In an embodiment of the invention, there exists a lower inner wall (2.9) presenting the lower portion of the emptied area within the body (2). The lower inner wall (2.9) is arranged parallel to the lower surface (2.2). The lower inner wall (2.9) serves a base for the expansion apparatus (E) so that the expansion apparatus (E) located inside the body (2) and used for raising the movable element (3) will elevate the movable element (3) to the preferred height.

In an embodiment of the invention, a movable element (3) is located in the opening which is made in the body (2) and surrounded by a front inner wall (2.6), preferably by two opposed side inner walls (2.7) and rear inner walls (2.8), wherein the lower portion of said opening is closed by the lower inner wall (2.9).

The movable element (3) is a component whose height can be elevated in the body (2) in case it is required to increase the intervertebral distance during the surgical operation. The movable element (3) has a size that allows it to be placed in the body (2), preferably being of a certain height. The movable element (3) consists of retainers (3.1) enabling it to be fixed inside the body (2), at least one toothed surface (3.2) contacting with the upper vertebra, and at least one protrusion (3.3) which is disposed in its lower surface and with which the expansion apparatus (E) contacts. The toothed surface (3.2) enables the movable element (3) to be attached in the upper vertebra. The protrusion (3.3) is the component with which the expansion apparatus (E) contacts during the elevation of the movable element (3), which is positioned in the body (2), in upward direction by means of the expansion apparatus (E). The user rotates the expansion apparatus (E) clockwise or counterclockwise by way of the protrusion (3.3), and thus making it raise. The retainers (3.1) at the sides of the movable element (3), a portion of which is preferably elevated in upward direction, are fitted in the lugs (3.11) without being raised inside the body (2). When the movable element (3) is elevated to the preferred height by means of the expansion apparatus (E), the retainers (3.1) are engaged in the barriers (3.10); and the retainer (3.1) at one side of the movable element (3) is fitted and fixed in the emptied area between the front inner wall (2.6) and front surface (2.4). In this embodiment of the invention, the retainers (3.1) are provided by shaping the edges of the movable element (3).

In another embodiment of the invention, the retainer (3.1) may be a component that is mounted in the movable element (3), wherein it enclosed by the movable element (3) and is mounted in the movable element (3) such that the movable element (3) will be located in the body (2) and prevented from being displaced.

In an embodiment of the invention, the rear surface (2.5) of the body (2) is provided with an inlet (2.13). The inlet (2.13) is formed by emptying a portion of the rear surface (2.5). When it is preferred to elevate the movable element (3) during the application, the expansion apparatus (E) is placed in the body (2) through the inlet (2.13), contacts with the protrusion (3.3) in the lower surface of the movable element (3), whereby the movable element (3) is raised until the barriers (2.10) disposed in the front inner wall (2.6) and rear inner wall (2.8).

The implanting process of an expandable cage (1) according to the invention is as follows: after the damaged intervertebral disc is removed, the region of the disc is cleaned. Subsequent to cleaning, the body (2) and the movable element (3) thereon are located between the vertebrae such that the front surface (2.4) of said body (2) will face towards the inside of the body. Afterwards, the expansion apparatus (E) is positioned inside the body (2) through the inlet (2.13) disposed in the rear surface (2.5) of the body (2) in accordance with the distance between the vertebrae. In such position, the expansion apparatus (E) is in contact with the protrusion (3.3) provided in the lower surface of the movable element (3). The expansion apparatus (E) is rotated clockwise or counterclockwise at a certain angle. With the rotation of the expansion apparatus (E), the protrusion (3.3) with which it is in contact, and hence the movable element (3) can be brought to the preferred height. After the movable element (3) is raised until the barriers (2.10) disposed in the front inner wall (2.6) and rear inner wall (2.8), it is fitted in the lugs (2.11) disposed on the side inner walls (2.7). When the movable element (3) is in this position, the upper portion of the retainers (3.1) at two opposed sides thereof is delimited by the barriers (3.10) while the lower portion of the other two opposed sides is delimited by the lugs (2.11), whereby it is locked in such position. After the preferred intervertebral distance is adjusted, the expansion apparatus (E) is retracted through the inlet (2.13) and the positioning of the expandable cage (1) between the vertebrae is thus completed.

In an embodiment of the invention, the component in which the rear inner wall (2.8) and the rear surface (2.5) are provided may be manufactured separately from the body (2). In this case, such component is mounted in the body (2) through the horizontal holes (2.14) disposed on the rear surface (2.5).

With an expandable cage (1) according to the invention, the movable element (3) can be locked between the vertebrae at the preferred height. The expandable cage (1) fills in the area between the two vertebra in which it is applied, and is fused with the bones, and thus enables the patients to continue their daily lives shortly after the implementation. The expandable cage (1) can be made of various materials, said materials being biocompatible. The materials of which the expandable cage (1) is made are also capable of carrying post-implementation loads.

An expandable cage (1) according to the invention differs from the cage designs used in the art due to its simple design, having a locking mechanism, ability to be applied in a short time, and allowing the patients to continue their daily lives immediately after the implementation.

The invention claimed is:

1. An expandable cage for fixing a distance between a pair of vertebrae during cervical surgical procedures, the expandable cage comprising:
   at least one body adapted to be positioned between the pair of vertebrae; and
   at least one movable element located on said at least one body and fitted in an opening of said at least one body by retainers disposed at sides thereof, said at least one movable element having a toothed surface adapted to contact an upper vertebrae of the pair of vertebrae, said at least one movable element having a protrusion at a lower portion thereof said at least one movable element having a height adjustable by pushing the protrusion with an expansion device.

2. The expandable cage of claim 1, wherein said at least one body has at least one upper surface, said at least one upper surface having spikes thereon, said at least one body having at least one lower surface with a tooth thereon, the at least one upper surface adapted to contact the upper vertebrae, the at least one lower surface adapted to contact a lower vertebrae of the pair of vertebrae, said at least one body having lateral surfaces at opposite sides thereof, said at least one body having at least one front surface facing toward and inside of said at least one body and at least one rear surface facing toward an outside of said at least one body.

3. The expandable cage of claim 2, wherein said at least one body has a front inner wall arranged parallel to the at least one front surface in the opening of said at least one body, the front inner wall having a thickness and a height that are less than a thickness and a height of said at least one front surface.

4. The expandable cage of claim 3, wherein the front inner wall has a barrier disposed thereon in a space between the front inner wall and the at least one front surface, said at least one movable element having one end engaged with the barrier when said at least one movable element is raised.

5. The expandable cage of claim 3, wherein said at least one body has a side inner wall having a lug and an insert, the side inner wall being joined perpendicular to the front inner wall and a rear inner wall, the side inner wall being parallel to the lateral surfaces.

6. The expandable cage of claim 5, wherein the lug extends upwardly from a lower portion of the side inner wall, the lug fixing said at least one movable element at a desired height.

7. The expandable cage of claim 6, wherein the retainers are fitted on the insert when said at least one movable element is positioned at a lower portion of the lug, the retainers being perpendicular to the lug and parallel to a lower inner wall.

8. The expandable cage of claim 2, wherein a rear inner wall is parallel to the rear surface, the rear inner wall having a barrier thereon.

9. The expandable cage of claim 2, wherein said at least one body has a lower inner wall at a lower portion of the opening within said at least one body, the lower inner wall being parallel to the at least one lower surface, the lower inner wall being a base for the expansion device such that the expansion device is removably received within said at least one body in order to elevate the at least one movable element to a desired height.

10. The expandable cage of claim 9, wherein said at least one movable element is surrounded by a front inner wall and by a pair of opposed side inner walls and by a rear inner wall, wherein a lower portion of the opening is closed by the lower inner wall.

11. The expandable cage of claim 1, further comprising:
    a barrier positioned so as to hinder an upward movement of upper portions of the retainers so as to fix the height of said at least one movable element.

12. The expandable cage of claim 1, wherein the expansion device contacts the protrusion during an elevation of said at least one movable element, the expansion device being rotatable in a clockwise direction and a counterclockwise direction.

13. The expandable cage of claim 1, wherein the retainers are respectively fitted to lugs when said at least one movable element is not raised in said at least one body.

14. The expandable cage of claim 1, further comprising:
    an inlet formed at a rear surface of said at least one body, said inlet removably receiving the expansion device.

15. The expandable cage of claim 1, wherein said at least one movable element is fitted in lugs disposed on side inner walls of said at least one body subsequent to being raised.

* * * * *